United States Patent
Nishimura et al.

(10) Patent No.: US 10,969,309 B2
(45) Date of Patent: Apr. 6, 2021

(54) VIRUS CONCENTRATION METHOD

(71) Applicant: KTEN BIO INC., Kobe (JP)

(72) Inventors: Naoyuki Nishimura, Nagata-ku (JP); Hidetomo Samori, Nagata-ku (JP)

(73) Assignee: KTEN BIO INC., Kobe (JP)

( * ) Notice: Subject to any disclaimer, the term of this patent is extended or adjusted under 35 U.S.C. 154(b) by 0 days.

(21) Appl. No.: 16/451,824

(22) Filed: Jun. 25, 2019

(65) Prior Publication Data

US 2020/0011774 A1 Jan. 9, 2020

(30) Foreign Application Priority Data

Jul. 3, 2018 (JP) .............................. JP2018-126772

(51) Int. Cl.
| | | |
|---|---|---|
| *C12N 7/02* | (2006.01) | |
| *G01N 1/40* | (2006.01) | |
| *C12Q 1/6806* | (2018.01) | |
| *C12Q 1/70* | (2006.01) | |

(52) U.S. Cl.
CPC ......... *G01N 1/4055* (2013.01); *C12Q 1/6806* (2013.01); *C12Q 1/70* (2013.01); *C12Q 2600/142* (2013.01)

(58) Field of Classification Search
None
See application file for complete search history.

(56) References Cited

FOREIGN PATENT DOCUMENTS

| JP | 2011-155919 A | | 8/2011 |
|---|---|---|---|
| JP | 2019037149 A | * | 3/2019 |

OTHER PUBLICATIONS

Bachrach et al., "Practical Procedures for the Purification of Bacterial Viruses," Applied Microbiology, vol. 22, No. 4 (Year: 1971).*
Caligur, "Dextran and Related Polysaccharides," BioFiles 3.10, 17 (Year: 2008).*
EPO Translation of JP2019037149A (Year: 2019).*
Bronson et al., "Concentration of Rous Sarcoma Virus from Tissue Culture Fluids with Polyethylene Glycol," Applied Microbiology, vol. 30, No. 3: 464-471 (Year: 1975).*
IASR (Infectious agents Surveillance Report), Dec. 2011, pp. 358-359, vol. 32.

* cited by examiner

*Primary Examiner* — M Franco G Salvoza
(74) *Attorney, Agent, or Firm* — Sughrue Mion, PLLC

(57) ABSTRACT

Provided is a method suitable for concentrating the viruses present in the environment, food or biomaterials in fields such as inspections for ensuring public or food safety and medical examinations, and reagents used therein.
By adding an optimum concentration of polysaccharide such as glycogen to polyethylene glycol (PEG) and optimizing the concentration of a salt to be added, the viruses suspended in an aqueous solution can be easily, rapidly and stably recovered at a high recovery rate.

5 Claims, No Drawings

VIRUS CONCENTRATION METHOD

TECHNICAL FIELD

The present invention relates to a method suitable for concentrating and detecting viruses (particularly pathogenic viruses) present in the environment, food materials or biomaterials, in fields of inspection for ensuring public safety and food safety, and further in the field of clinical practice, and reagents used therein.

BACKGROUND ART

Various viruses are known to induce diarrhea in human, including norovirus, rotavirus, adenovirus, astrovirus, coronavirus and hepatitis A virus.

In the field of clinical practice, daily monitoring and vigilance against viruses are necessary for coping with the annual epidemics of influenza virus, the worldwide spread of human immunodeficiency virus, and the future pandemic risks of many viruses such as highly pathogenic influenza virus and Ebola virus.

Among the viruses causing food poisoning, norovirus (hereinafter referred to as NV) is the cause of food poisoning that frequently occur in winter and spring. NVs are classified into 7 genotypes (GI-GVII), among which GI, GII and GIV are known to infect humans to induce gastroenteritis. In recent years, GII (particularly GII.4) has caused the majority of norovirus outbreaks. In Japan about 70% of infectious food poisoning cases are caused by NV, with 10-30 thousand cases reported every year, but the actual number of NV infections is estimated to be about 100 times larger than the reported number.

The potential transmission routes of NV are: (1) sewage→shellfish→human, (2) food workers→utensils/food materials→human, (3) human→human, human→facility environment→human. The major infection route used to be (1), but most of the recent NV infections have been caused by the human-mediated routes (2) and (3).

Such high spreading potential is attributed to the following features of NV: (1) because NV is an RNA virus and has a high mutation rate, and because protection against NV infection is based on intestinal mucosal immunity, the immunity generated by the first infection is not effective against reinfection or is short-lived; (2) a large amount of NV is shed not only in the feces but also in vomit ($10_5$-$10_9$ viruses/g in patient feces, $10_3$-$10_7$ viruses/g in patient vomit); (3) infected individuals continue to shed NV over a long period, even after their symptoms disappear (it has been reported that the virus had been shed over 3 weeks in adults and more than 1 month in infants); (4) many infected individuals do not develop any symptoms (asymptomatic infection) but still shed sufficient amount of NV in their feces to cause human infection; (5) the virus is highly contagious, showing an infection rate of 50% after exposure to 100-1,000 NVs; (6) the virus can survive for long periods in the environment (the estimated survival periods when stored in a dry state are 2 months and 1 month at 4□ and 20□, respectively).

Under these circumstances, in Japan, in the revision made in June 2008 for "Hygienic Control Manual for Large-Scale Cooking Facilities" (Appendix of Notification No. 85 of Food Sanitation Division, Environmental Health Bureau, Ministry of Health and Welfare on Mar. 24, 1997, final revision: Article 1 of Notice No. 0610 of the Department of Food Safety), which is targeted to cooking facilities preparing more than 300 dishes of a single menu at a time or more than 750 meals per day (large-scale cooking facilities), the Ministry of Health, Labour and Welfare additionally advised "NV stool examination" and "withdrawal of NV-infected individuals from cooking procedures".

Nevertheless, NV infection still accounts for about ⅔ of food poisoning cases and occur at a wide range of places, including facilities at which food is directly handled, e.g. restaurants, caterers, hotels and manufacturing plants, as well as offices, schools, hospitals, sales stores and home.

Therefore, for preventing NV infections, in addition to conventional NV stool examinations (individual examination), it should be extremely effective to perform NV testing at food-handling sites or places suspected of NV contamination, as well as wide-area (environmental) inspection and monitoring.

Regarding inspections conducted for preventing NV infections, in the field of food inspection, the targets of inspection are utensils used for food processing (e.g. cutting boards, knives), food handlers themselves (e.g. their clothing, hands) and food materials. Meanwhile, in the field of environmental inspection, equipment and supplies in various facilities are inspected, including toilet bowls, floors, doorknobs, handrails and slippers at toilet facilities, which are expected to be the most highly contaminated areas.

If a rapid, simple and high-sensitivity NV testing method can be established in the field of food inspection or environmental inspection, the method can also be applied to other viruses or to the clinical field. In the clinical field, the testing targets would be those related to the environment, such as medical instrument or equipment, as well as samples derived from medical staff or patients.

In the actual virus testing procedure, first, areas suspected of virus contamination are wiped with a tool such as a swab impregnated with a buffer (e.g. phosphate buffer), physiological saline or distilled water.

The collected virus is suspended in the buffer, physiological saline or distilled water that has been used to impregnate the wiping tool and subsequently concentrated either by centrifuging the virus suspension after mixing it with a concentration liquid containing polyethylene glycol (hereinafter referred to as PEG) or through direct ultracentrifugation of the virus suspension.

For example, "Detection Method for Norovirus" (Notice No. 1105001 from the Food Inspection and Safety Division, dated Nov. 5, 2003, final revision Notice No. 0514004 from the Food Inspection and Safety Division, dated May 14, 2007, www.mhlw.go.jp/topics/syokuchu/kanren/kansai/dl/031105-1a.pdf) prepared by the Ministry of Health, Labour and Welfare in Japan, describes the concentration procedure as follows:

"Concentration Method using Polyethylene Glycol (1) . . . to the centrifuged supernatant, add polyethylene glycol 6,000 and NaCl so as to give concentrations of 8% and 2.1 g/100 ml, respectively, stir gently and leave overnight at 4° C. in a refrigerator, or stir for 2 hours at room temperature.

↓Perform refrigerated centrifugation at 5,000-12,000 rpm for 20 minutes.

(2) Suck the supernatant with an aspirator, a syringe or the like to leave only the sediment. Remove moisture around the tube wall with a sterile filter paper. Lightly rinse the tube wall with PBS(−) twice and subsequently remove moisture completely with a filter paper.

(3) Suspend the sediment in 200 µl of DDW and use this for extracting the viral RNA. If the suspension contains too much impurity, conduct refrigerated centrifugation at 10,000 rpm for 20 minutes and use the resulting supernatant for RNA extraction."

The concentrated virus can be checked by amplifying and detecting the nucleic acid in the virus (DNA or RNA) or by detecting the antigens present at the viral surface.

For detecting the nucleic acid in the virus, genetic tests are performed either by directly using the virus or extracting and purifying the nucleic acid (DNA or RNA) therefrom. Then, if the test target is DNA, the DNA is amplified by PCR or the like, and if the test target is RNA, the RNA is amplified either directly or after conversion into DNA by a reverse transcription (RT) reaction. The analysis is conducted in real time using e.g. the probe method or by melting curve analysis (MCA) or agarose electrophoresis after the amplification.

However, it was difficult to recover the virus stably at a high recovery rate by the conventional PEG precipitation method, and its long, complicated operation procedure was not suited for smooth processing of a large number of samples. On the other hand, the ultracentrifugation method required an expensive equipment and could handle only a small number of samples at a time, resulting in poor work efficiency.

Recently, attempts were made to improve the recovery rate e.g. by adding beef extract to PEG (e.g. a document provided below: IASR Vol. 32 p. 358-359: December 2011 issue), but the recovery rate was rather unstable and could only reach around 40% at maximum. Moreover, the method had a disadvantage in terms of work efficiency, such as keeping the sample in a refrigerator overnight before centrifugation.

Furthermore, in NV detection, when the samples to be used for detection are concentrated by ultracentrifugation or PEG precipitation, impurities may remain in the samples to inhibit PCR reaction and prevent norovirus detection. As examples of such impurities, saccharides such as mucus and humic acid, proteins, dyes and glycogen are exemplified (patent publication number 2011-155919).

Consequently, the conventional PEG precipitation method can only give a detection sensitivity of about 10,000 NV/swab, which is not sufficient for testing or monitoring contamination by a virus as highly contagious as NV, which is known to infect 50% of the people exposed to 100-1,000 viruses.

PRIOR ART DOCUMENTS

Patent Documents

[Patent Document 1] Patent Publication No. 2011-155919

Non-Patent Documents

IASR (Infectious agents Surveillance Report) Vol. 32 p. 358-359: December 2011 issue

SUMMARY OF THE INVENTION

Problem to be Solved by the Invention

The viruses collected with a wiping tool (e.g. a swab) is suspended in the buffer, physiological saline or distilled water used to impregnate the wiping tool and subsequently concentrated by centrifugation of the virus suspension mixed with a PEG solution or through direct ultracentrifugation of the virus suspension. In the conventional PEG precipitation method, it was difficult to recover the virus stably at a high recovery rate, and the long, complicated operation procedure was not suited for smooth processing of a large number of samples. On the other hand, the ultracentrifugation method required an expensive equipment and could handle only a small number of samples at a time, resulting in poor work efficiency.

Means for Solving the Problem

The purpose of the invention is to provide a PEG-based concentration liquid for easily, rapidly and stably recovering viruses suspended in a buffer, physiological saline or distilled water at a high recovery rate. This enables easy, rapid, stable and efficient concentration of viruses present in the environment, food materials or biomaterials.

Concentrated viral genes (nucleic acids: DNA or RNA) can be amplified to a high degree by PCR or RT-PCR or the like. The amplified DNA or RNA can be quantitatively detected with high sensitivity e.g. by using a fluorescent probe. Detection of genes in the virus generally involves extraction and purification of the nucleic acid from the virus before the gene amplification. If the sample could be directly (without purification) added to the reaction, it should be advantageous in terms of convenience and speed.

Such easy, rapid, high-sensitivity detection and monitoring of a virus (particularly a pathogenic virus) present in the environment, food materials or biomaterials should enable effective prevention of virus transmission and greatly contribute to prevention of epidemics.

The nucleic acid extracted from cells, fungi, bacteria or biomaterials containing them is concentrated and purified by a method called ethanol precipitation, wherein a salt such as sodium acetate, ammonium acetate, lithium chloride or sodium chloride and an organic solvent such as ethanol are added to the aqueous solution containing the nucleic acid to form a precipitation. In this method, glycogen is sometimes added as a coprecipitating agent.

Since viruses are typically negatively charged like nucleic acids, we assumed that addition of glycogen would also be effective in PEG-based virus concentration. Our assumption proved correct, and glycogen was effective to a certain degree.

We also found that polysaccharides other than glycogen were also effective. The glycogen concentration suited for virus concentration was at least 1000 times higher than that typically used for recovering nucleic acid by ethanol precipitation, and the suitable concentration of a salt (e.g. sodium chloride) added to PEG was lower than that typically added in the conventional PEG precipitation method for concentrating NV. Moreover, polysaccharides have been reported to inhibit PCR in the above-mentioned document, but when we conducted RT-PCR by directly (without RNA purification) adding a NV sample concentrated using a polysaccharide-containing PEG solution to the reaction, no inhibition was observed, as long as the concentration of the coexisting salt was within the optimum range. Thus, the present invention provides a virus concentration method comprising adding a liquid containing polyethylene glycol, salt and polysaccharide, either individually or in a mixed state, to a liquid in which the virus is suspended, and subsequently conducting centrifugal operation to concentrate the virus.

For concentrating NV using the conventional PEG solution, centrifugation needs to be carried out at 5,000-12,000 rpm for 20 minutes under cooling. The inventors found that, by using the polysaccharide-containing PEG solution (hereinafter referred to as polysaccharide-PEG solution), norovirus of GI or GII genotype could be stably recovered at a high rate from distilled water or physiological saline at a shorter spin time of within 10 minutes (around 5-10 minutes) and without cooling.

When concentrating NV using the conventional PEG solution, the sample needs to be kept in a refrigerator overnight or stirred for 2 hours at room temperature before centrifugation. The inventors found that, by using the polysaccharide-PEG solution, norovirus of GI or GII genotype could be stably recovered at a high recovery rate without cooling and without allowing the NV suspension to stand for more than 10 minutes after mixing it with the polysaccharide-PEG solution, and completed this invention.

Thus, the present invention also provides a virus concentration method wherein the standing before centrifugation and the centrifugation are conducted without cooling. In addition, the present invention also provides a virus concentration method wherein the centrifugal operation comprises conducting centrifugation for within 10 minutes after standing for within 10 minutes.

A polysaccharide capable of reaching a suspended state in the PEG solution can probably be used as the polysaccharide to be added to the PEG solution.

Non-limiting examples of the polysaccharide are glucose-derived amylopectin, curdlan, glycogen, cellulose, α-cellulose, dextrin, N-acetyl glucosamine-derived chitin and fructose-derived inulin, and a mixture thereof can also be used.

Among the above-mentioned polysaccharides, glycogen, dextrin and inulin are recommended, and glycogen is most recommended.

The amount of glycogen to be added is much higher than that typically used for ethanol precipitation of DNA (final concentration: 0.000008%). The optimum concentration is 0.01% or higher, particularly 0.02-0.08%, as final concentration in a liquid obtained by adding the PEG solution to the virus suspension.

As in the conventional PEG precipitation method, PEG with a molecular weight of 6,000 is used at a final concentration of 8%, but this is a non-limiting example and can be changed as needed.

When crystallizing proteins using PEG, sodium chloride, lithium chloride, ammonium sulfate or lithium sulfate is added. The inventors believe that any of them can be used in this method, but these are non-limiting examples and can be changed to other salts as needed.

Regarding the amount of sodium chloride added to PEG, the final salt concentration is typically around 3% in the conventional PEG precipitation method for concentrating NV. However, a lower salt concentration is appropriate when using the polysaccharide-PEG solution, i.e. a final concentration of 0.021% or higher (final concentration) but lower than 6.6%, preferably 0.066-2.1% (final concentration).

The virus suspension can be centrifuged immediately after mixing it with the polysaccharide-PEG solution but preferably left to stand for about 10 minutes. The standing temperature is not particularly limited to but preferably room temperature for the sake of convenience.

Acceleration, temperature and time of centrifugation are not particularly limited to but are preferably 10,000 G or higher, room temperature or lower, and 5 minutes or longer but within 10 minutes, respectively.

The virus to be concentrated is not particularly limited to but includes all DNA and RNA viruses including diarrhea viruses causing food poisoning, such as norovirus, sapovirus, rotavirus, adenovirus and astrovirus, as well as enterovirus and hepatitis virus.

Potential test materials are the environment, food materials and clinical samples, but the invention is particularly suited for testing NV in the environment.

The sample concentrated by the virus concentration method of the present invention can be directly added, without purification, to the reagent for PCR to amplify and detect the nucleic acid in the virus.

A known PCR reaction mixture can be used for the invention. For example, reagents and primers used in the Detection Method for Norovirus (issued by the Ministry of Health, Labour and Welfare in Japan) can be used.
(e.g. Notice No. 1105001 from the Food Inspection and Safety Division, dated Nov. 5, 2003, final revision Notice No. 0514004 from the Food Inspection and Safety Division, dated May 14, 2007 www.mhlw.go.jp/topics/syokuchu/kanren/kansai/dl/031105-1a.pdf)

Advantageous Effects of the Invention

The polysaccharide-PEG solution according to the present invention enables easy, rapid, stable, efficient and stable concentration of a trace amount of virus attached to the environment, food materials or biomaterials. By directly (i.e. without nucleic acid purification) using the virus concentrated by the present method in (RT)-PCR, the gene can be easily and rapidly amplified to a high degree. Moreover, by combining the present method with real-time detection using a specific fluorescent probe for the target amplification product, the virus present in the sample can be quantitatively detected with high sensitivity and high specificity.

Based on the above, the use of the method of the present invention for detecting or monitoring viruses, particularly highly contagious viruses that are easily transmitted from human to human either directly or via the environment to cause severe symptoms in human, such as norovirus and influenza virus, can contribute to safety and sanitation, particularly at food-handling sites or healthcare sites.

In addition, the method of the present invention can also be applied to the development and assessment of antiviral disinfectants or confirmation of disinfection. By combining the present method with an effective disinfectant, further protection against viral infection can be expected.

DESCRIPTION OF THE EMBODIMENTS

Example 1

Various polysaccharides were added to the PEG solution to examine their effectiveness in concentration of NV. About 1,000 NVs of GI or GII genotype were added to 400 μl of distilled water, and an equal amount of 16% PEG 6,000 solution (containing sodium chloride) containing 0.025% of various polysaccharides was added and left to stand at room temperature for 10 minutes. Then, centrifugation was conducted at 14,000 G for 5 minutes in a microcentrifuge set at 20° C. After sucking and removing the centrifuged supernatant, a self-made sample treatment reagent was added to the sediment and heated at 85° C. for 3 minutes. To the heat-treated sample, a self-made reaction mixture containing primers for detecting GI and GII and probes with 3'-ends labeled with GI- and GII-specific fluorescent dyes was added to conduct real-time RT-PCR. Table 1 shows the recovery rate of samples concentrated with each polysaccharide-PEG solution. That is, it represents the recovery rate calculated by comparing the Ct value (the number of cycles in which the fluorescence signal exceeds the threshold during real-time RT-PCR) when NV is added directly and after concentration to the RT-PCR system. For each polysaccharide, the average recovery rate of duplicate assays was calculated. The results indicate that the addition of glycogen yielded the highest recovery rate, recovering 70% or more of GI or GII NV added. The next highest recovery rate was 30%, which was achieved with either dextrin or inulin. Amylopectin, curdlan, cellulose, α-cellulose and chitin yielded recovery rates of around 10%. All of these were polysaccharides reaching a suspended state in a PEG solution. Meanwhile, when a polysaccharide completely soluble in PEG solution (i.e. lignin) was added, no rise in the fluorescence signals specific to GI and GII could be observed, as in the case of polysaccharide-free PEG solution.

used in Example 1, we decreased the amount of sodium chloride added to the glycogen-containing PEG solution in 1/√10-fold steps, starting from 3% (final concentration), which is the concentration typically used in the conventional PEG precipitation method for concentrating NV, and examined the concentrating effect. The results are shown in Tables 3 and 4. For each concentration, the median recovery of quadruplicate, quintuplicate or sextuplicate assays was calculated, and its ratio against the median recovery of the highest recovery group is shown in the Tables. The effect of salt concentration on the recovery was larger for GI (Table 3) compared to GII (Table 4), and the suitable range of salt concentration tend to be narrower at higher glycogen concentrations. For concentrating both genotypes, a salt concentration of 0.021% or higher but lower than 6.6%, particularly 0.066-2.1% (final concentration) was considered optimum.

TABLE 1

"Comparison of recovery rates of NV suspended in distilled water achieved by adding various polysaccharides to PEG solution"

| Saccharide | Amylopectin | Curdlan | Glycogen | Cellulose | α-Cellulose | Dextrin | Chitin | Inulin | Lignin |
|---|---|---|---|---|---|---|---|---|---|
| GI recovery rate (%) | 11 | 5.3 | 98 | 5.2 | 4.5 | 43 | 14 | 39 | 0 |
| GII recovery rate (%) | 7.1 | 17 | 73 | 15 | 13 | 32 | 14 | 30 | 0 |

Example 2

Using glycogen, which was most effective in NV recovery among the polysaccharides added to the PEG solution, another experiment was conducted using the same system as that used in Example 1 to determine the optimum amount to be added. Starting from 0.000008% (final concentration), which is the amount typically used in ethanol precipitation of DNA, we increased the amount of glycogen in 10-fold steps. A high concentrating effect was observed at 1000-fold or higher concentrations. Then, we sought the optimum concentration within the range of 0.0025-0.16%, the result of which is shown in Table 2. For each concentration, the median recovery of quintuplicate assays was calculated, and its ratio against the median recovery of the highest recovery group is shown in the Table. A higher concentration of glycogen was required for concentrating GII compared to GI, but for concentrating both genotypes, a glycogen concentration of 0.01% or higher, particularly 0.02-0.08% (final concentration) was considered optimum.

TABLE 2

"Recovery rates achieved when NV suspended in distilled water was concentrated using various concentrations of glycogen as an example of polysaccharide to be added to PEG solution"

| | Final concentration of glycogen (%) | | | | | | | |
|---|---|---|---|---|---|---|---|---|
| | 0.16 | 0.08 | 0.04 | 0.02 | 0.01 | 0.005 | 0.0025 | 0 |
| GI recovery ratio | 0.43 | 0.71 | 1 | 0.82 | 0.60 | 0.41 | 0.34 | 0.03 |
| GII recovery ratio | 1 | 0.83 | 0.88 | 0.81 | 0.80 | 0.58 | 0.54 | 0.03 |

Example 3

In a PEG solution containing the glycogen concentration selected in Example 2 (final concentration of 0.01-0.08%), the amount of sodium chloride was changed to determine the optimum amount of this salt. Using the same system as that

TABLE 3

"Recovery rates of NV GI suspended in distilled water achieved with various sodium chloride concentration in glycogen-containing PEG solution"

| Final concentration of glycogen | Final concentration of sodium chloride (%) | | | | | | | |
|---|---|---|---|---|---|---|---|---|
| (%) | 6.6 | 2.1 | 0.66 | 0.21 | 0.066 | 0.021 | 0.007 | 0 |
| 0.01 | 0.61 | 1 | 0.81 | 0.95 | 0.73 | 0.68 | 0.91 | 0.12 |
| 0.02 | 0.70 | 0.99 | 0.78 | 1 | 0.75 | 0.72 | 0.67 | 0.23 |
| 0.04 | 0.02 | 1 | 0.71 | 0.65 | 0.60 | 0.53 | 0.59 | 0.17 |
| 0.08 | 0 | 1 | 0.95 | 0.72 | 0.85 | 0.66 | 0.57 | 0.53 |

TABLE 4

"Recovery rates of NV GII suspended in distilled water achieved by various sodium chloride concentration in glycogen-containing PEG solution"

| Final concentration of glycogen | Final concentration of sodium chloride (%) | | | | | | | |
|---|---|---|---|---|---|---|---|---|
| (%) | 6.6 | 2.1 | 0.66 | 0.21 | 0.066 | 0.021 | 0.007 | 0 |
| 0.01 | 0.23 | 1 | 0.82 | 0.81 | 0.89 | 0.72 | 0.44 | 0.02 |
| 0.02 | 0.07 | 1 | 0.76 | 0.73 | 0.65 | 0.37 | 0.12 | 0.11 |
| 0.04 | 0 | 1 | 0.98 | 0.92 | 0.81 | 0.52 | 0.30 | 0.11 |
| 0.08 | 0 | 0.56 | 1 | 0.87 | 0.75 | 0.55 | 0.41 | 0.24 |

Example 4

To a NV suspension, an equal amount of 16% PEG 6,000 solution containing 0.025% glycogen and 1.2% sodium chloride was added, and the suspension was centrifuged in a microcentrifuge set at 20° C. or 4° C. at 14,000 G for 1, 5, 10 or 20 minutes. The sediments recovered after centrifugation were tested in the same system as that used in Example 1 to compare the concentrating effect. The results are shown in Table 5. For each centrifugation condition, the median recovery rate of quadruplicate assays was calculated. The results greatly differed from that observed under the centrifugation condition (refrigerated centrifugation at 5,000-12,000 rpm for 20 minutes) used for concentrating NV using the conventional PEG solution. Centrifugation at 20° C. (simulating centrifugation at room temperature) yielded a recovery rate similar to that achieved at 4° C., and the recovery rate achieved with a spin time of 10 minutes was comparable to that achieved with 20 minutes.

TABLE 5

"Effects of centrifugation temperature and time on recovery rate; NV-suspended distilled water was mixed in equal amounts with a solution (hereinafter referred to as GPEG solution) prepared by adding optimum concentrations of sodium chloride and glycogen to 6% PEG 6,000 solution and concentrated by centrifugation (14,000 G) at 4° C. or 20° C."

| | Spin temperature (□) | | | | | | | |
|---|---|---|---|---|---|---|---|---|
| | 20 | 20 | 20 | 20 | 4 | 4 | 4 | 4 |
| Spin time (minutes) | 1 | 5 | 10 | 20 | 1 | 5 | 10 | 20 |
| GI recovery rate (%) | 50 | ≥100 | ≥100 | ≥100 | 29 | ≥100 | ≥100 | ≥100 |
| GII recovery rate (%) | 43 | ≥100 | ≥100 | ≥100 | 18 | 86 | ≥100 | ≥100 |

Example 5

When concentrating NV using the conventional PEG solution, the NV suspension mixed with the PEG solution need to be kept in a refrigerator overnight or stirred 2 hours at room temperature. In this example, the NV suspension was mixed with the PEG solution used in Example 4 and, either immediately after mixing or after standing at 20° C. for 3,5,10 or 20 minutes, it is centrifuged in a microcentrifuge set at 20° C. at 14,000 G for 5 minutes. The recovery rates are shown in Table 6. The recovery rate for each standing time was calculated as the median recovery of octuplicate assays. The recovered sediments were tested in the same system as that used in Example 1 to compare the concentrating effect. The results showed that GI could be sufficiently recovered without any standing, while GII was recovered at the highest rate when centrifuged after a standing time of about 10 minutes.

TABLE 6

"Effect of pre-centrifugation standing time on recovery rate; the NV-suspended distilled water mixed with an equal amount of GPEG solution was allowed to stand at 20° C. for various time periods"

| Standing time (minutes) | 0 | 3 | 5 | 10 | 20 |
|---|---|---|---|---|---|
| GI recovery rate (%) | ≥100 | ≥100 | ≥100 | ≥100 | ≥100 |
| GII recovery rate (%) | 70 | 92 | 82 | ≥100 | ≥100 |

Example 6

In order to demonstrate the applicability of the present invention to viruses other than NV, we tested whether hepatitis B virus (HBV) could be concentrated according to the invention. A 1000-IU HBV suspension was mixed with an equal amount of the PEG solution used in Example 4 and allowed to stand at 20° C. for 10 minutes before it was centrifuged in a microcentrifuge set at 20° C. at 14,000 G for 5 minutes. The resulting sediment was suspended in 200 µl of PBS and further subjected to nucleic acid extraction using QIAamp MinEluteVirus Spin Kit (QIAGEN). Meanwhile, for preparing a calibration curve, 3 different amounts of HBV, i.e. 100, 1000 and 10000 IU, were added to 200 µl of PBS and subsequently subjected to nucleic acid extraction. Concentration of the test samples and extraction from the samples were both performed in triplicates for each sample. The resulting nucleic acid extracts were subjected to real-time PCR to determine the Ct values, and the viral loads were calculated from the calibration curve. As shown in Table 7, the average recovery rate was 59%, which demonstrates the applicability of the present invention to a virus other than NV.

TABLE 7

"Hepatitis B virus (HBV) concentrating effect"

| | Name | Ct | Virus titer (IU) | average |
|---|---|---|---|---|
| Concentrated test sample | Sample1 | 27.85 | 553.4 | 590.4 |
| | Sample2 | 27.88 | 544.0 | |
| | Sample3 | 27.54 | 673.8 | |
| Calibration curve preparation sample | 100 IU 1 | 30.74 | 85.49 | |
| | 100 IU 2 | 30.48 | 100.9 | |
| | 100 IU 3 | 30.70 | 87.60 | |
| | 1000 IU 1 | 26.66 | 1194 | |
| | 1000 IU 2 | 26.55 | 1281 | |
| | 1000 IU 3 | 26.73 | 1144 | slope |
| | 10000 IU 1 | 22.59 | 16524 | −3.564 |
| | 10000 IU 2 | 24.29 | 5511 | intercept |
| | 10000 IU 3 | 23.66 | 8300 | 37.62 |

The invention claimed is:

1. A virus concentration method comprising:
   (a) adding a concentration liquid containing polyethylene glycol, salt and glycogen, either individually or in a mixed state, to a liquid in which the virus is suspended,
   (b) subsequently centrifuging to concentrate the virus, and
   wherein the glycogen has a final concentration of glycogen of 0.02-0.08% in the concentration liquid.

2. The virus concentration method according to claim 1, wherein the salt added to the concentration liquid is selected from among sodium chloride, lithium chloride, ammonium sulfate, and lithium sulfate.

3. The virus concentration method according to claim 2, wherein the sodium chloride has a final concentration of sodium chloride of 0.021% or higher but lower than 6.6% when the final concentration of glycogen is 0.02-0.08%.

4. The virus concentration method according to claim 1, wherein the centrifuging comprises allowing to stand before centrifugation and the centrifugation does not comprise cooling.

5. The virus concentration method according to claim 1, wherein the centrifuging comprises conducting centrifugation for within 10 minutes after allowing to stand for within 10 minutes.

* * * * *